United States Patent

Blümel et al.

[11] Patent Number: 4,759,328
[45] Date of Patent: Jul. 26, 1988

[54] METHOD AND CIRCUIT ARRANGEMENT FOR DETECTING THE READINESS FOR OPERATION OF AN OXYGEN MEASUREMENT PROBE

[75] Inventors: Thomas Blümel, Schmitten; Bernhard Lukas, Raunheim; Wolfgang Reisch, Biebergemünd-Bieber; Eberhard Mausner, Bad Soden, all of Fed. Rep. of Germany

[73] Assignee: VDO Adolf Schindling AG, Frankfurt am Main, Fed. Rep. of Germany

[21] Appl. No.: 107,570

[22] Filed: Oct. 9, 1987

[30] Foreign Application Priority Data

Oct. 30, 1986 [DE] Fed. Rep. of Germany ....... 3637029
Dec. 24, 1986 [DE] Fed. Rep. of Germany ....... 3644472

[51] Int. Cl.⁴ ............................................. F02D 41/14
[52] U.S. Cl. ..................................... 123/440; 123/489
[58] Field of Search ......................... 123/440, 489, 589; 204/425, 426

[56] References Cited

U.S. PATENT DOCUMENTS

| 3,938,479 | 2/1976 | Oberstadt | 123/489 |
| 4,132,193 | 1/1979 | Takase et al. | 123/440 |
| 4,140,086 | 2/1979 | Schnurle et al. | 123/440 |
| 4,208,993 | 6/1980 | Peter | 123/440 |
| 4,226,221 | 10/1980 | Asano | 123/440 |
| 4,345,562 | 8/1982 | Drews et al. | 123/489 X |
| 4,393,841 | 7/1983 | Drews et al. | 123/440 |
| 4,485,786 | 12/1984 | Kashimura | 123/440 |
| 4,671,244 | 6/1987 | Clement et al. | 123/440 X |
| 4,698,765 | 10/1987 | Abe et al. | 123/489 X |

Primary Examiner—Willis R. Wolfe
Attorney, Agent, or Firm—Martin A. Farber

[57] ABSTRACT

In a method for detecting the readiness for operation of a oxygen measurement probe which is arranged in the exhaust duct of an internal combustion engine and serves together with a regulating device to regulate the preparation of the mixture for the internal combustion engine, the output voltage of the oxygen measurement probe is integrated with an integration time constant which is dependent on the internal resistance of the oxygen measurement probe. The rate of change of the output voltage is measured. Above a predetermined value of the rate of change, readiness for operation is noted. In a circuit arrangement for the carrying out of the method, there is connected to the output of the oxygen measurement probe the input of an integrator whose output is connected via an analog-to-digital converter to the input of a microcomputer. Also there can be fed to an integrator an initial value which lies in a central part of the operating range of the output voltage of the integrator.

28 Claims, 3 Drawing Sheets

METHOD AND CIRCUIT ARRANGEMENT FOR DETECTING THE READINESS FOR OPERATION OF AN OXYGEN MEASUREMENT PROBE

FIELD AND BACKGROUND OF THE INVENTION

The present invention relates to a method and a circuit arrangement for detecting the readiness for operation of an oxygen measurement probe which is arranged in the exhaust duct of an internal combustion engine and together with a regulation device serves to regulate the preparation of the mixture for the internal combustion engine.

In order to obtain an exhaust which is as free of injurious substances as possible, control devices for internal combustion engines are known in which the oxygen content in the exhaust duct is measured and evaluated. For this purpose oxygen measuring probes, so-called lambda probes, are known which operate in accordance with the principle of ion conduction through a solid electrolyte as a result of a difference in oxygen partial pressure and which give off a voltage signal which corresponds to the oxygen partial pressure present in the exhaust gas and exhibits a sudden change in voltage upon transition from deficiency of oxygen to an excess of oxygen.

The internal resistance of the known oxygen measurement probes is, however, so great at low temperatures that the signal given off by the oxygen measurement probe upon a cold start and during the warm-up phase of the internal combustion engine cannot be evaluated. In known devices for regulating the preparation of the mixture therefore a control which is independent of the output signal of the oxygen measurement probe is provided up to the region of readiness for operation of the oxygen measurement probe. Only after the oxygen measurement probe has reached its readiness for operation is its output signal used for regulating the fuel-air ratio.

In a known method for monitoring the readiness for operation of an oxygen measurement probe, the oxygen measurement probe is acted on by a test voltage having a constant mean value of the voltage which can be produced by the oxygen measurement probe. The resultant voltage at the output of the probe is fed as control variable of the readiness for operation to two comparison devices for comparison with an upper and a lower probe value corresponding in each case to a minimum output voltage of the oxygen measurement probe, and a mixture control device is connected or disconnected via a timing member, in the place of the mixture regulating device, in accordance with the output signal of the comparison device.

In another known method for the monitoring of the readiness for operation of an oxygen measurement probe, in which a voltage resulting under the influence of the behavior of the probe is also scanned by two comparison circuits with threshold voltages and then evaluated, a constant reference voltage is connected in opposition for the detection of the probe internal resistance which characterizes the readiness of the probe, the threshold voltages of the comparison circuits connected in opposition to the output voltage produced hereby lie by predetermined difference values above and below the reference voltage, in which connection the output signals given off by the comparison circuits and corresponding to a total of three logical switch states are processed by a subsequent evaluation circuit for switching between regulation and control or vice versa.

It is an object of the present invention to indicate a method for the detecting of the readiness for operation of an oxygen measurement probe which can be carried out reliably with simple and economical circuit arrangements. Furthermore, by the invention it is to be made possible to adapt the recognition by simple means to the conditions prevailing at the time.

SUMMARY OF THE INVENTION

According to the invention, there is provided a method wherein the output voltage of the oxygen measurement probe is integrated with an integration time constant which is dependent on the internal resistance of the oxygen measurement probe, the rate of change of the output voltage is measured and readiness for operation is detected above a predetermined value of the rate of change.

By the method of the invention a simple reliable detection of the readiness for operation of the oxygen measurement probe is possible. It can also be used to monitor the oxygen measurement probe during operation.

A further development of the method of the invention is that readiness for operation is furthermore only detected as long as a second predetermined value of the rate of change is not exceeded. This further development makes it possible to recognize a short-circuit of the oxygen measurement probe.

In accordance with another embodiment of the method of the invention, an initial value is fed to the integrator, for which purpose one input of the integrator is preferably substantially short-circuited for a short time.

In this way assurance is provided that, even during the warm-up phase, a signal is integrated as a function of the internal resistance of the oxygen measurement probe, so that the internal resistance can be measured with it.

Another further development of the invention contemplates that, after the start of the internal combustion engine, measurements are repeatedly made until the rate of change has increased to or above the predetermined value.

In this way it is made possible for readiness for operation to be recognized as soon as possible after the oxygen measurement probe has reached the required temperature.

The preestablished value or preestablished values can be adapted particularly easily to the conditions in the individual case if, in accordance with another development of the invention, they are taken from a storage whose content is variable.

One advantageous circuit arrangement for the carrying out of the method of the invention is that, to the output of the oxygen measurement probe (1) there is connected the input of an integrator whose output is connected via an analog-to-digital converter (14) to the input (15) of a microcomputer (16).

With suitable programming a microcomputer which is in any event used for regulating purposes can be used to carry out the method of the invention by adding merely a few electronic components.

One advantageous development of the circuit arrangement of the invention consists in the fact that the input of the integrator can furthermore be connected via a controllable switch (20) with constant potential and that a signal is fed to the controllable switch (20) from an output (17) of the microcomputer (16). The controllable switch is preferably a transistor.

Another advantageous development of the invention is that the integrator is formed of an operation amplifier (6), the inverting input of which forms the input of the integrator and is connected via a capacitor (9) to the output of the operational amplifier (6), and that the non-inverting input is acted on by a constant voltage. In this way the operating point of the integrator is fixed.

It can be provided in this connection that a balanceable resistor (5, 21) is arranged between the inverting input of the operation amplifier (6) and the controllable switch (20) as well as between the inverting input of the operation amplifier (6) and the output of the oxygen measurement probe. Furthermore, the capacitor (9) can be connected to the output of the operation amplifier (6) via a voltage divider (7, 8).

Finally, in accordance with a further development, the capacitor is so dimensioned that the integration time constant, with the oxygen measurement probe ready for operation, exerts substantially no influence on the regulating characteristic.

In this way, it is possible to use the circuit arrangement of the invention itself for the forwarding of the probe signal to the microcomputer. However, it is also possible to effect the recognition of readiness for operation and the preparation of a signal in separate circuits.

The invention permits numerous embodiments.

It is also an object of the present invention to improve this method and the circuit arrangement.

Further according to the method of the invention, the integrator is fed with an initial value which lies within a central portion of the operating region of the output voltage of the integrator. In this way a dependable recognition of the readiness for operation is possible regardless of whether a rich or lean mixture is present in the warm-up phase and what voltage the oxygen measurement probe gives off.

According to the invention, the rate of change can be determined in simple fashion by providing two voltage thresholds which form a hysteresis for the evaluation of the output voltage of the integrator, and provide that time between a feeding of an initial value and an exceeding of one of the voltage thresholds by the initial voltage serve as measure of the rate of change.

Another further development of the method consists therein that, during the operation of the internal combustion engine, the feeding of the initial value and the measuring of the rate of change are effected repeatedly. In this way it is possible to monitor the oxygen measurement probe not only during the warm-up phase but also during operation.

One development of the method of the invention consists therein that, after the start of the internal combustion engine, the feeding of the initial value and measurements of the rate of change are effected repeatedly, until the rate of change has increased to or above the predetermined value.

In this case the feeding of the initial value and the measurement of the rate of change can be repeated after predetermined time intervals. In this connection the time intervals can be fixed or variable.

However, it can also be provided that the feeding of the initial value and the measuring of the rate of change are triggered in each case by a sudden change in the output signal of the oxygen measurement probe.

In order to make measurements possible also if a change takes place between rich and lean mixture during the warm-up phase for a long period of time, the feeding of the initial value and the measuring of the rate of change can furthermore be triggered if after a predetermined period of time there is no sudden change in the initial voltage.

One advantageous circuit arrangement for the carrying out of the method of the invention is characterized by the fact that to the output of the oxygen measurement probe (1) there is connected the input of an integrator whose output is connected via an analog-to-digital converter (14) to the input (15) of a microcomputer (16), that the input of the integrator can furthermore be connected via a controllable switch (31) to constant potential, that a signal is fed from an output (17) of the microcomputer (16) to the controllable switch (31), and that the constant potential corresponds to the initial value.

BRIEF DESCRIPTION OF THE DRAWINGS

With the above and other objects and advantages in view, the present invention will become more clearly understood in connection with the detailed description of preferred embodiments, when considered with the accompanying drawing, of which.

DETAILED DESCRIPTION OF THE PREFERRED EMBODIMENTS

Figure 1:
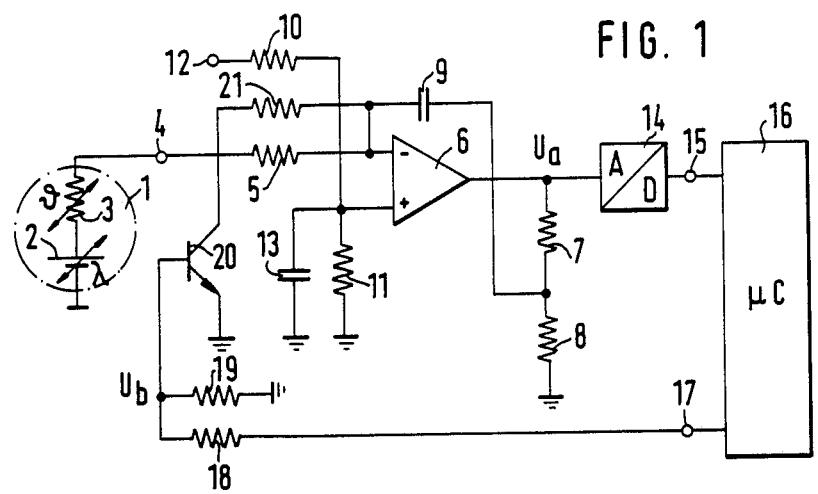
FIG. 1 is a wiring diagram of a circuit for the carrying out of the method of the invention.

The oxygen measurement probe 1 which is known per se is shown in FIG. 1 merely as a voltage source 2 whose voltage is dependent on the percentage of oxygen and whose internal resistance 3 is dependent on temperature. The output voltage of the oxygen measurement probe 1 is fed via a terminal 4 and a balancing resistor 5 to the inverting input of an operation amplifier 6.

Together with a voltage divider 7, 8 and a capacitor 9, the operation amplifier 6 forms an integrator, known per se. Via another voltage divider 10, 11 half of the operating voltage fed at 12 is fed to the non-inverting input of the operation amplifier 6. For the suppressing of voltage peaks the non-inverting input is furthermore connected via a capacitor 13 to ground potential. The resistor 11 of the additional voltage divider 10, 11 is developed so that it can be adjusted so that the voltage present on the non-inverting input can be adjusted.

The output of the operation amplifier 6, which at the same time forms the output of the integrator, is connected via an analog-to-digital converter 14 to an input 15 of a microcomputer 16.

An output 17 of the microcomputer 16 is connected via a voltage divider 18, 19 to the base of a transistor 20. The emitter of the transistor 20 is connected to ground potential and the collector is connected via a balancing resistor 21 to the inverting input of the operation amplifier 6.

In known manner the microcomputer 16 is designed by means of a stored program and corresponding setting members not shown in detail to regulate for complete combustion of the amount of fuel fed to the internal combustion engine. For this purpose, the amount injected is, for instance, suitably regulated by control of the system pressure or by control of the period of injection. Such systems are known and need not be described in detail in connection with the present invention.

In the case of the embodiment shown, the microcomputer 16 is designed by a further program for the operation of the circuit shown in FIG. 1. For this purpose, as will be explained in further detail with reference to FIG. 2, after a starting of the internal combustion engine and when the lambda probe is therefore cold and has a high internal resistance, the transistor 20 (FIG. 1) is brought for a short time into the conductive state. In this way the inverting input of the operation amplifier 6 assumes ground potential so that the output voltage assumes the upper limit of the control region. The resistor 21 has such a small value that the recharging of the capacitor 9 necessary for this is possible within a short time.

Figure 2B:
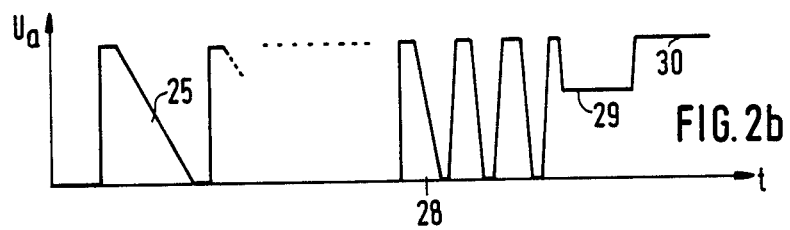
FIGS. 2a, 2b and 2c are voltage-time diagrams of a few voltages and signals occurring with the circuit arrangement of FIG. 1.
Figure 2C:
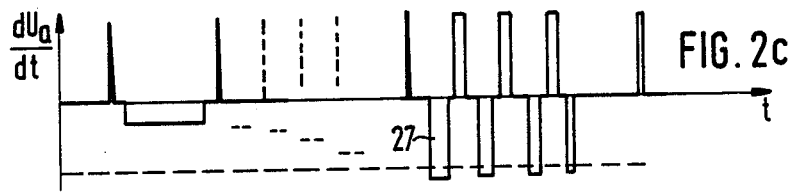
Figure 2A:
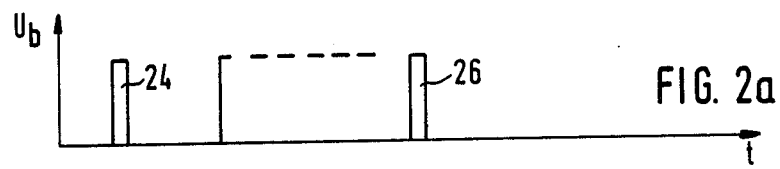

After the rear flank of the pulse 24, the transistor 21 is again non-conductive so that the output voltage of the operation amplifier 6 which is shown in FIG. 2b adjusts itself, with corresponding recharging of the capacitor 9, to the value predetermined by the output voltage of the oxygen measurement probe. Since in most cases of operation the internal combustion engine receives too rich a mixture after the starting, and therefore there is a deficiency of oxygen, the output voltage Ua drops from its maximum value to zero in accordance with the function 25 shown in FIG. 2b. Since in the cold state the internal resistance 3 of the oxygen measurement probe has a large value, the drop in the output voltage Ua takes place very slowly. In a circuit developed in actual practice, for instance, periods of time of an order of magnitude of 20 ms were, for instance, necessary for this.

By a suitable program in the microcomputer 16 (FIG. 1) the rate of change of the output voltage Ua is determined. For further interpretation therefore the first derivative with respect to time of the signal shown in FIG. 2b is plotted in FIG. 2c. The dotted horizontal line represents the rate of change at which the operating temperature is considered reached. Since this is not the case after the measurement after the first pulse 24, further pulses are given off by the microcomputer 16, they not being shown in detail. By the heating of the oxygen measurement probe which has taken place in the meantime, the rate of change of the output voltage Ua after the pulse 26 is greater than the preestablished value (see curve portion 27, FIG. 2c).

As soon as the rate of change exceeds the predetermined value, switching is effected in the microcomputer, from a control which takes place in accordance with stored fields of characteristic curves to a regulation. From this time 28 on, the time constant determined by the internal resistance and the additional balancing resistance 5 as well as the capacitor 6 is so small that the regulating characteristic of the regulating circuit established by the microcomputer, the probe, the circuit arrangement of the invention, the internal combustion engine and the setting members corresponding thereto is fundamentally not affected by the integrator. Aside from less steep flanks and the sign, the output voltage Ua corresponds to the amplified output voltage of the probe. If there is an interruption of the feed line from the probe to the integrator then the time constant of the integration member increases substantially, so that the previously existing output voltage Ua continues to exist for a long period of time after the interruption (see signal section 29). In the event of a short-circuit of the oxygen measurement probe, however, the output voltage Ua increases to its maximum value (see signal section 30). Both can be evaluated in the microcomputer.

Figure 3:
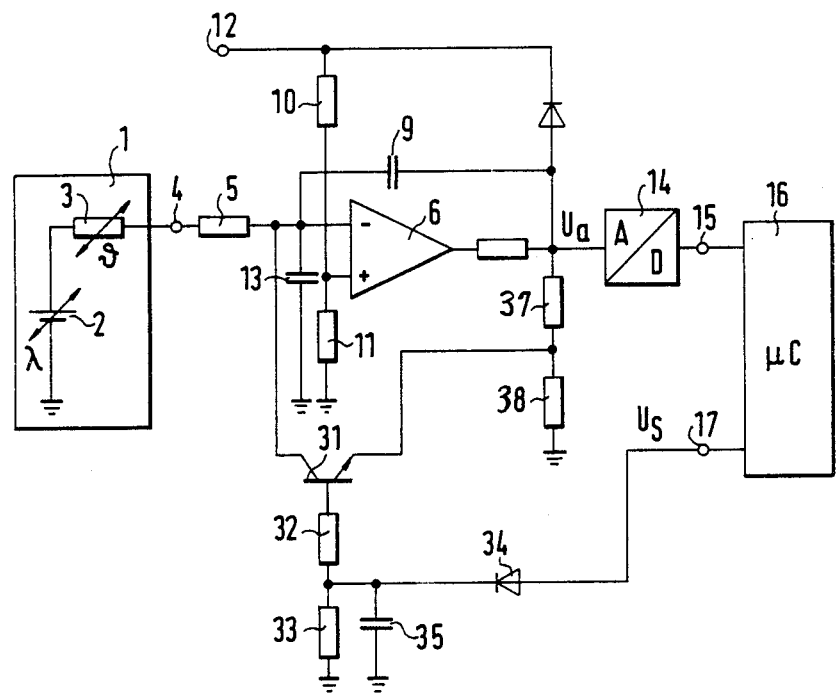
FIG. 3 is another wiring diagram of a circuit arrangement for the carrying out of a method according to the invention.

The oxygen measurement probe 1 which is known per se is shown in FIG. 3 merely as a source of voltage 2 the voltage of which is dependent on the percentage of oxygen and the internal resistance 3 of which is dependent on temperature. The output voltage of the oxygen measurement probe 1 is fed via a terminal 4 and a resistor 5 to the inverting input of an operation amplifier 6.

Together with a capacitor 9, the operation amplifier 6 forms an integrator, known per se. Via a voltage divider 10, 11 a part of the operating voltage fed at 12 is fed to the non-inverting input of the operation amplifier 6. For the suppressing of voltage peaks the non-inverting input is furthermore connected via a capacitor 13 to ground potential. The resistor 11 of the additional voltage divider 10, 11 is developed so that it can be adjusted so that the voltage present on the non-inverting input can be adjusted.

The output of the operation amplifier 6, which at the same time forms the output of the integrator, is connected via an analog-to-digital converter 14 to an input 15 of a microcomputer 16.

A control voltage Us is fed from an output 17 of the microcomputer 16 to the base of a transistor 31 which connects the output of the voltage divider 37, 38 to the inverting input of the operation amplifier 6. In this connection, the circuit consisting of the resistors 32, 33, the diode 34 and the capacitor 35 serves for the production of the bias voltage for the transistor 31.

In known manner, the microcomputer 16 is designed by means of a stored program and corresponding setting members, not shown in detail, to regulate for complete combustion the amount of fuel fed to the internal combustion engine. For this purpose, the amount injected is, for instance, suitably regulated by control of the system pressure or by control of the period of injection. Such systems are known and need not be described in detail in connection with the present invention.

Figure 4A:
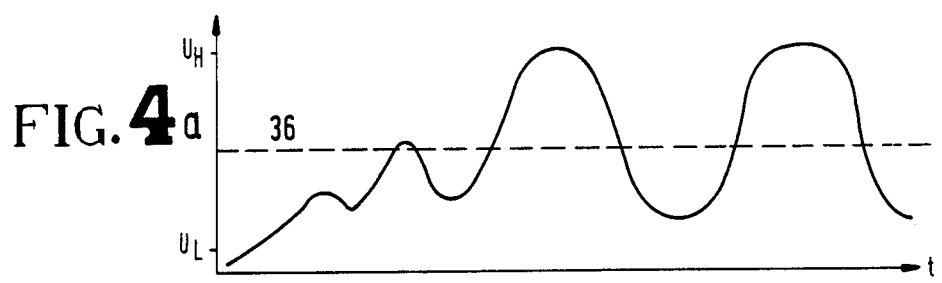
FIGS. 4a to 4e are voltage-time diagrams of a few voltages and signals occurring with the circuit arrangement of FIG. 3.
Figure 4B:
Figure 4C:
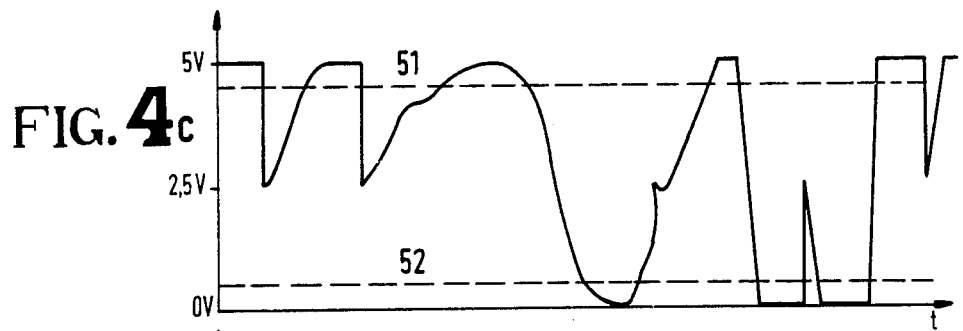
Figure 4D:
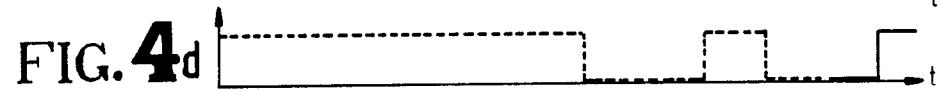
Figure 4E:
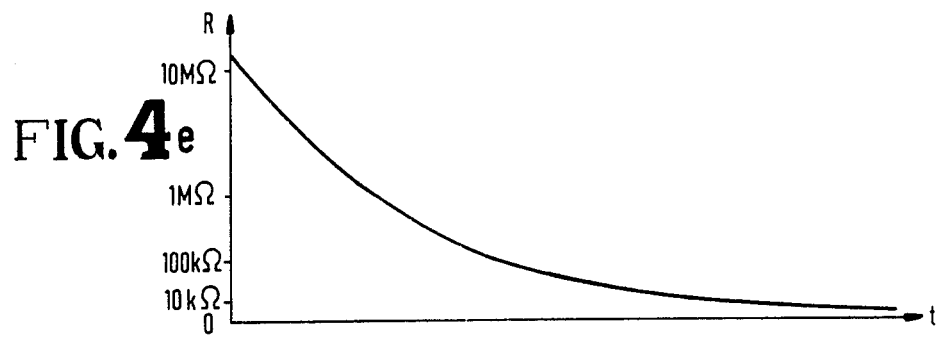

In the case of the embodiment shown, the microcomputer 16 is designed by another program for the operation of the circuit shown in FIG. 3. This will be explained in further detail with reference to FIGS. 4a to 4e. In this connection there is shown in each case as time diagram:

In FIG. 4a the output voltage of the oxygen measurement probe, in FIG. 4b the control voltage Us given off by the microcomputer, in FIG. 4c the output voltage of the integrator, in FIG. 4d the evaluated output voltage of the integrator and in FIG. 4e the internal resistance of the oxygen measurement probe.

The output voltage shown in FIG. 4a of the oxygen measurement probe assumes, in the event of an excess of oxygen and therefore too lean a mixture, low values, for instance 0.1 V. In case of a deficit of oxygen, the oxygen measurement probe gives off a voltage the maximum value of which is about 0.9 V. The threshold for the integrator is between these two values and is indicated as dashed line in FIG. 2a.

Within a first period of time after the start of the internal combustion engine with the oxygen measurement probe cold, the oxygen measurement probe shows an extremely high internal resistance (see FIG. 4e). The output voltage is then not evaluatable. Therefore, during this period of time and in the event of an interruption in the feed lines to the oxygen measurement probe, a regulator is operated for the preparation of the mixture in the sense of a control based on stored fields of characteristic lines.

After a start of the internal combustion engine and when, therefore, the oxygen measurement probe is cold and has a high internal resistance, the transistor 31 (FIG. 3) is controlled in the conductive condition for a short time by a pulse 41. As a result, the output voltage of the operation amplifier 6 assumes a value which lies in the middle of the operating range.

After the rear flank of the pulse 41 the transistor 31 is again non-conductive so that the output voltage of the operation amplifier 6 shown in FIG. 4c increased to 5 V. Due to the high internal resistance of the oxygen measurement probe, the output voltage of the operation amplifier 6 increases relatively slowly. The time between the pulse 41 and an exceeding of the voltage threshold 51 by the output voltage of the operation amplifier 6 is measured. If the measured time is above a preestablished value, it is noted thereby that the oxygen measurement probe is not yet ready for operation.

Upon the next pulse 42 (FIG. 4b) the output voltage of the operation amplifier 6 rises even more slowly since here, on the one hand, the internal resistance of the oxygen measurement probe is still relatively high and, on the other hand, its output signal is in the vicinity of the threshold 36 of the integrator. Accordingly switching is not yet effected to a regulator operation even after this pulse. Thereupon a deficit of oxygen occurs temporarily so that the output voltage of the oxygen measurement probe assumes higher values. The output signal of the operation amplifier 6 accordingly drops and comes below the voltage threshold 52. In this connection it may furthermore be mentioned that the voltage thresholds 51 and 52 and a comparison of the output voltage of the operation amplifier 6 with these voltage thresholds in the microcomputer are carried out by a suitable program and with stored values for the voltage thresholds 51, 52.

After the pulse 43 given off by the microcomputer 16, there is also as yet no rapid increase in voltage since the pulse falls approximately into a change in sign of the oxygen measurement probe. In the meantime, however, the oxygen measurement probe is heated to such an extent that its internal resistance has become small. After the pulse 44, therefore, the output voltage of the operation amplifier 6 drops rapidly back to zero and drops below the threshold 52 within the preestablished period of time. It is concluded from this that the oxygen measurement probe is ready for operation, a switch is made from a control to a regulation. After the sudden change in the output voltage of the oxygen measurement probe due to an enrichment of the mixture, the output voltage of the operation amplifier 6 exceeds the upper threshold 51. Upon the following pulse 45 the output voltage is again placed at the average value of 2.5 V and then rises rapidly again to the upper value of 5 V.

The thresholds 51, 52 produce a hysteresis in the manner that the signal to be evaluated last for the regulation assumes a first value H when the output voltage of the operation amplifier 6 exceeds the upper threshold 51 and assumes the second value L when the threshold 52 is dropped below. FIG. 4d shows this signal, it being indicated in dotted line up to the time 46 since it is used for regulation only as from that time on.

Since the feeding of the initial value for the integrator in no way impairs the production of the signal represented in FIG. 4b and thus the regulating function, the testing of readiness for operation of the oxygen measurement probe can be effected not only in a warm-up phase but also continuously during operation so that errors which occur, for instance an interruption of the feed line, can be indicated immediately. A switching from the regulator to operation in line with a control can then also take place.

The pulses 41 to 45 can be given off regularly by the microcomputer 16; however, a triggering by sudden changes in the output voltage of the oxygen measurement probe is also possible.

As used herein, the term "flanks" refers to leadeing and trailing edges of signal pulses.

We claim:

1. A method for detecting readiness for operation of an oxygen measurement probe located in an exhaust duct of an internal combustion engine, the probe being operative with a regulation device to regulate a fuel-air mixture for the internal combustion engine, the method comprising the steps of integrating an output voltage of the oxygen measurement probe to provide an integrated output voltage, an integration time constant of the integration being dependent on the internal resistance of the oxygen measurement probe, measuring a changing speed of the integrated output voltage, and detecting the readiness for operation above a predetermined value of the changing speed.

2. The method according to claim 1, wherein the step of detecting the readiness for operation is accomplished as long as a second predetermined value of changing speed of integration is not exceeded.

3. The method according to claim 1, further comprising a feeding of an initial value to an integrator for the integration.

4. The method according to claim 3, wherein the integrating is initiated by substantially short-circuiting one input of the integrator for a short time.

5. The method according to claim 2, further comprising a feeding of an initial value to an integrator for the integration.

6. The method according to claim 5, wherein the integrating is initiated by substantially short-circuiting one input of the integrator for a short time.

7. The method according to claim 2, further comprising a repeating of the integrating and measuring method steps after starting of the internal combustion engine until the changing integration speed has increased at least to the predetermined value.

8. The method according to claim 1, further comprising storing the predetermined value by means of a memory whose content is variable.

9. The method according to claim 1, wherein
the integrating is accomplished with an integrator, the method further comprising the step of
feeding the integrator with an initial value which lies within a central portion of an operating region of an output voltage of the integrator.

10. The method according to claim 9, wherein
the changing integration speed is determined by providing two voltage thresholds which form a hysteresis for evaluation of the output voltage of the integrator; the method further comprising
employing a time elapsed between the feeding of the initial value and an exceeding of one of the voltage thresholds by the initial voltage as a measure of the changing integration speed.

11. The method according to claim 9, further comprising
a repeating, during the operation of the internal combustion engine, of the steps of feeding the initial value and the steps of measuring the changing integration speed.

12. The method according to claim 10, further comprising
a repeating, during the operation of the internal combustion engine, of the steps of feeding the initial value and the steps of measuring the changing integration speed.

13. The method according to claim 9, further comprising
repeating, after starting of the internal combustion engine, the step of feeding the initial value and the step of measuring the changing integration speed, until change of integration speed has increased to at least the predetermined value.

14. The method according to claim 10, further comprising
repeating, after starting of the internal combustion engine, the step of feeding the initial value and the step of measuring the changing integration speed, until change of integration speed has increased to at least the predetermined value.

15. The method according to claim 11, further comprising
repeating the feeding of the initial value and the measuring of the changing integration speed after predetermined time intervals.

16. The method according to claim 12, further comprising
repeating the feeding of the initial value and the measuring of the changing integration speed after predetermined time intervals.

17. The method according to claim 11, further comprising
triggering the feeding of the initial value and the measuring of the change of integration speed by a sudden change in the output signal of the oxygen measurement probe.

18. The method according to claim 12, further comprising
triggering the feeding of the initial value and the measuring of the change of integration speed by a sudden change in the output signal of the oxygen measurement probe.

19. The method according to claim 17, further comprising
triggering the feeding of the initial value and the measuring of the changing integration speed if, after a predetermined period of time, there is no sudden change in the initial voltage.

20. A circuit for detecting readiness for operation of an oxygen measurement probe located in an exhaust duct of an internal combusion engine, the probe being operative with a regulation device to regulate a fuel-air mixture for the internal combustion engine, the circuit comprising
an integrator, an analog-to-digital converter, and a microcomputer; and wherein
an output of the oxygen measurement probe is connected to an input of the integrator, an output of the integrator being connected via the analog-to-digital converter to the input of the microcomputer.

21. The circuit according to claim 20, further comprising
a controllable switch; and wherein
the input of the integrator is connected via the controllable switch to a constant potential, the switch being operated in respose to a signal fed to the controllable switch from an output of the microcomputer.

22. The circuit according to claim 21, wherein
the controllable switch is a transistor.

23. The circuit according to claim 20, wherein
the integrator comprises an operation amplifier and a capacitor, the inverting input of the amplifier serving as the input of the integrator and being connected via the capacitor to an output of the operational amplifier, a non-inverting input of the amplifier being provided with a constant voltage.

24. The circuit according to claim 23, further comprising
a first resistor connected between the inverting input of the operation amplifier and the controllable switch, and
a second resistor connected between the inverting input of the operation amplifier and the output of the oxygen measurement probe.

25. The circuit according to claim 23, further comprising
a voltage divider connecting the capacitor to the output of the operation amplifier.

26. The circuit according to claim 24, further comprising
a voltage divider connecting the capacitor to the output of the operation amplifier.

27. The circuit according to claim 23, wherein
said capacitor is so dimensioned that an integration time constant, with the oxygen measurement probe ready for operation, exerts substantially no influence on the regulating characteristic.

28. The circuit according to claim 20, further comprising
a voltage divider and a controllable switch connected via the divider between input and output terminals of the integrator; and wherein
a signal is fed from an output of the microcomputer to operate the controllable switch.

* * * * *